(12) United States Patent
Gurtner et al.

(10) Patent No.: US 8,652,123 B2
(45) Date of Patent: Feb. 18, 2014

(54) METHODS AND DEVICES FOR IMPROVING THE APPEARANCE OF TISSUE

(76) Inventors: Geoffrey C. Gurtner, Stanford, CA (US); Kenneth N. Horne, San Francisco, CA (US); Drew A. Hoffmann, Portola Valley, CA (US); Gordon Saul, Palo Alto, CA (US)

( * ) Notice: Subject to any disclaimer, the term of this patent is extended or adjusted under 35 U.S.C. 154(b) by 557 days.

(21) Appl. No.: 12/231,547

(22) Filed: Sep. 2, 2008

(65) Prior Publication Data

US 2010/0057056 A1    Mar. 4, 2010

(51) Int. Cl.
*A61B 18/18* (2006.01)
*A61F 2/00* (2006.01)
*A61M 35/00* (2006.01)

(52) U.S. Cl.
USPC ............... 606/9; 607/101; 604/289; 604/290

(58) Field of Classification Search
USPC .............. 604/164.01, 543; 606/9; 607/101
See application file for complete search history.

(56) References Cited

U.S. PATENT DOCUMENTS

| | | | |
|---|---|---|---|
| 6,470,216 B1 * | 10/2002 | Knowlton | 607/101 |
| 7,217,265 B2 * | 5/2007 | Hennings et al. | 606/9 |
| 2005/0251120 A1 * | 11/2005 | Anderson et al. | 606/20 |
| 2007/0093755 A1 * | 4/2007 | Koos et al. | 604/164.01 |
| 2008/0188835 A1 * | 8/2008 | Hennings et al. | 604/542 |

* cited by examiner

*Primary Examiner* — Melanie Hand
(74) *Attorney, Agent, or Firm* — Jens E. Hoekendijk (57) ABSTRACT

Cellulite is treated by severing septae, which interconnects the skin with the underlying muscle. The septae may be severed in connection with a liposuction procedure or independent of a liposuction procedure.

6 Claims, 14 Drawing Sheets

METHODS AND DEVICES FOR IMPROVING THE APPEARANCE OF TISSUE

BACKGROUND OF THE INVENTION

The present invention is directed to methods and devices for improving the appearance of tissue such as skin.

A known method of improving the appearance of tissue by removing fat is liposuction. Liposuction has become a widely accepted procedure for removing undesirable localized fat tissue, especially in areas that may be unresponsive to diet or exercise. This procedure is effective in removing excess accumulations of fat from various parts of the body such as the face, neck, waist, buttocks, thighs, inner upper thighs, knees, ankles, lower legs and upper arms.

Body fat varies in structure and composition in different regions of the body. Much of the subcutaneous fat in a normal, healthy human is generally arranged to form a thin blanket-like layer. In some areas of the body fat cells exist in large subcutaneous deposits.

The most common liposuction technique uses a blunt tip cannula positioned between the skin and muscle. Through an incision site, the cannula is repeatedly thrust radially while suction from a vacuum source is transmitted down the shaft of the cannula to the distal opening(s). As adipose tissue is freed it is aspirated through one or more holes in the side of the cannula. By controlling the quantity and location of adipose tissue removal, an enhanced surface contour or reduction in volume can be achieved.

One problem with conventional liposuction is that the mobility of the cannula is often limited by septae, which are fibrous connections between the skin and muscle layers. These septae cannot be easily severed by blunt liposuction cannulae, hence, the path of least resistance for the cannula is in tunnels or passageways in between the septae. In areas where the septae are dense the ability to access all the desired fat can be limited, especially further from the incision site. Consequently, many physicians will access the same area from two incision sites to try and address fat made inaccessible by septae. However, in practice many liposuction practioners still identify areas where excess fat exists but cannot be removed.

Another method of improving the appearance of tissue is to reduce the dimpling effect of cellulite. Cellulite is believed to be caused by the same fibrous tissue or septae which hamper liposuction procedures. One method of reducing the dimpled appearance of cellulite is to cut the septae using a needle having a sharp tip. The needle is dragged through tissue numerous times so that the sharp tip of the needle cuts the septae.

A problem with the above described method for reducing the appearance of cellulite is that the needle is highly inefficient when the desired treatment area is large. For example, a 10 cm by 10 cm area of skin, which is common in terms of the distribution of cellulite on an adult human, will likely contain 100 to 300 septae. Further, given the size of the needle and the distribution of septae, a 10 cm by 10 cm area of skin would require numerous incision sites in order to cut all the septae in that area. Multiple incision sites are undesirable to the patient, and time consuming for the physician.

SUMMARY OF THE INVENTION

The present invention provides devices and methods for improving the appearance of tissue. In particular, the present invention is directed to methods and devices for performing liposuction and methods and devices for cutting septae which interconnects skin and muscle.

In a first aspect of the present invention, a tissue cutting device is provided which is coupled to a liposuction cannula. The cutting element is movable from a stored position to a cutting position so that the user may elect when to cut tissue. As mentioned above, a problem with conventional liposuction is that the mobility of the cannula is limited to passageways or tunnels that are defined by septae. The septae can be difficult to penetrate or cut especially with blunt-tip cannula. The cutting element of the present invention permits the user to cut tissue adjacent to the cannula without removing the cannula from the incision site. In this manner, the user can position the liposuction wand adjacent to an area where the user desires to remove additional fat deposits that cannot be accessed due to tissue such as septae. The cutting element is then used to selectively cut tissue and, in particular, the septae adjacent to the cannula. The cutting element is then retracted such that tissue not intended to be cut is unaffected. The cannula may then be moved so that the distal tip is positioned in the area where the tissue has been cut and the user then accesses the area having additional fat deposits with the cannula. The cannula can be made to be flexible to facilitate navigation into new areas of tissue.

In another aspect of the present invention, an independent cutting element is deployed through the suction opening of a liposuction cannula. The cutting element may also be removable from the suction lumen so that the user may decide when and if the cutting element is to be used. The cutting element may also be rotatable within the suction lumen and may have surface features, such as a screw-type exterior, which help to draw material proximally through the lumen when the element is rotated.

In a further aspect of the present invention, the cutting device is configured to capture tissue, such as septae, which are oriented substantially perpendicular to the skin.

In another aspect of the present, the cutting element is housed is a housing or a tissue capturing element in a manner which protects the cutting element from exposure to undesired tissue.

In another aspect of the present invention, a housing which protects the cutting element and the cutting element are independently controlled. This enables the user to capture tissue, such as septae, and assess whether to cut or not before actuating the cutting element. For example, some septae manifest themselves on the skin surface as cellulite dimples when manipulated. If a captured septae did not manifest itself on the skin surface, the physician could elect not to actuate the cutting element. Checking for surface manifestation of the captured tissue will also prevent blood vessels and nerves from being unintentionally cut, since these may not manifest themselves on the skin surface.

In another aspect of the present invention, a cutting device may be provided which has an element which deflects upon application of a threshold force. The element may help to distinguish the relatively robust septae from softer structures such as blood vessels and nerves. Softer tissues may not be able to exert the same forces on the element and will deform in a manner which permits the softer tissues to flow around the element rather than being captured by the element. Once the element has been deflected, the device may either automatically cut the tissue trapped by the element or the device may include an indicator which notifies the user that the element has been deflected.

In another aspect of the present invention, a cutting device may be provided which has an electrical element which differentiates between fibrous septae and structures undesirable to be cut such as vessels and nerves by means of electrical characteristics. Tissue desired to be cut such as fat and septae have different electrical characteristics, for example impedance, when compared to vessels and nerves. The device may either automatically cut the tissue captured by the element based on its electrical characteristics or the device may include an indicator which notifies the user of the type of tissue or simply the un-interpreted electrical characteristic data. In cases where tumescence is utilized, it may be advantageous to use non-conductive fluids such as dextrose (e.g. D5W) rather than saline to facilitate differentiation of tissue structures.

In another aspect of the present invention, the cutting element can deliver RF energy to facilitate cutting of the tissue. Additionally, the RF energy will promote coagulation of any vessels which are bleeding.

In still another aspect of the present invention, the cutting device has the ability to provide the user with direct visualization of the cutting area. For example, the cutting device can be mated with a fiberscope or have a video-capable microchip (e.g. CMOS or CCD) contained in the distal tip. Direct visualization enables the user to see what is captured by the cutting device before electing whether or not to cut the tissue.

These and other aspects of the present invention will become apparent from the following description of the preferred embodiments.

DESCRIPTION OF THE PREFERRED EMBODIMENTS

Figure 1:
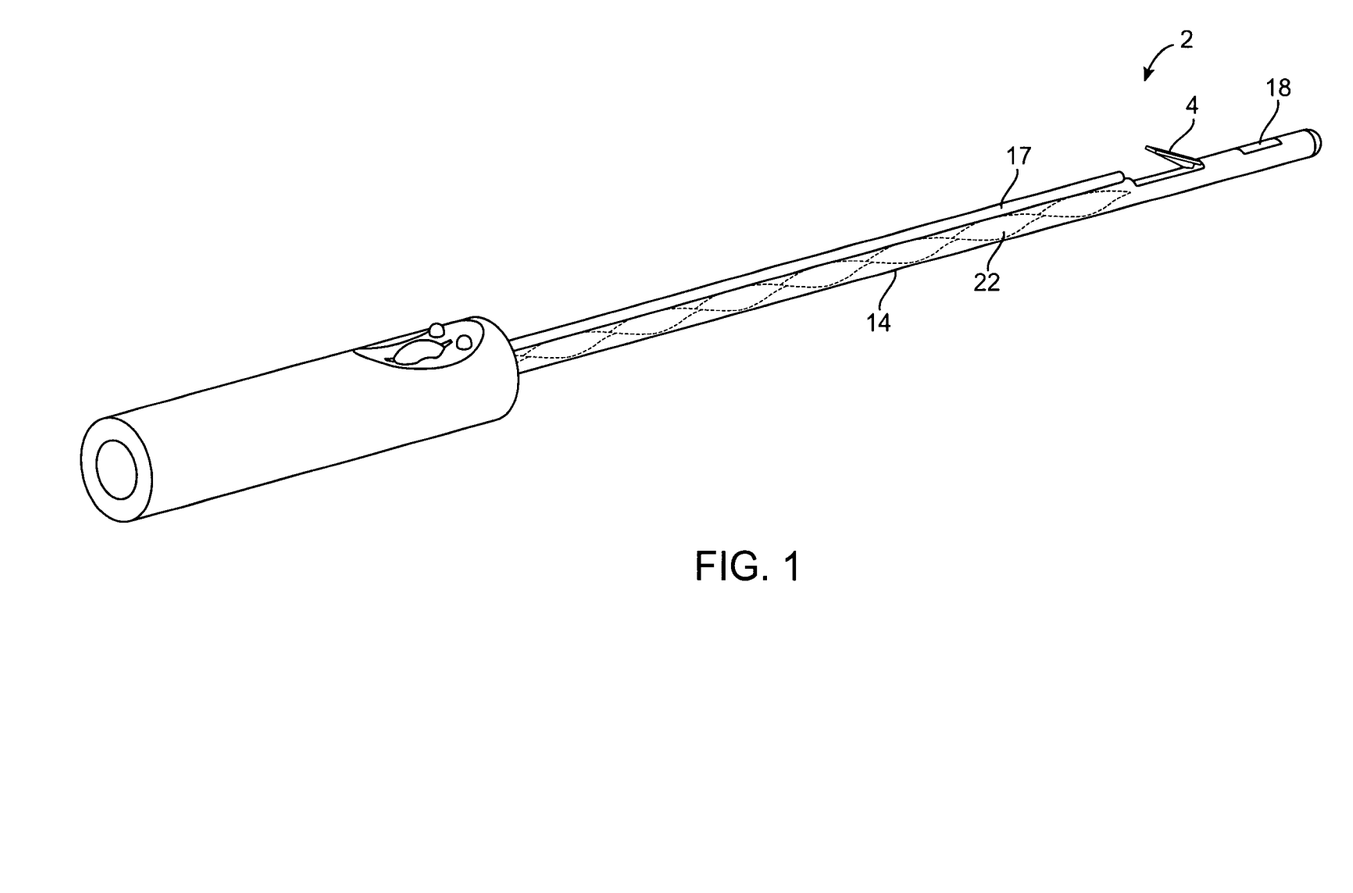
FIG. 1 shows a device for cutting tissue that can also perform liposuction
Figure 2:
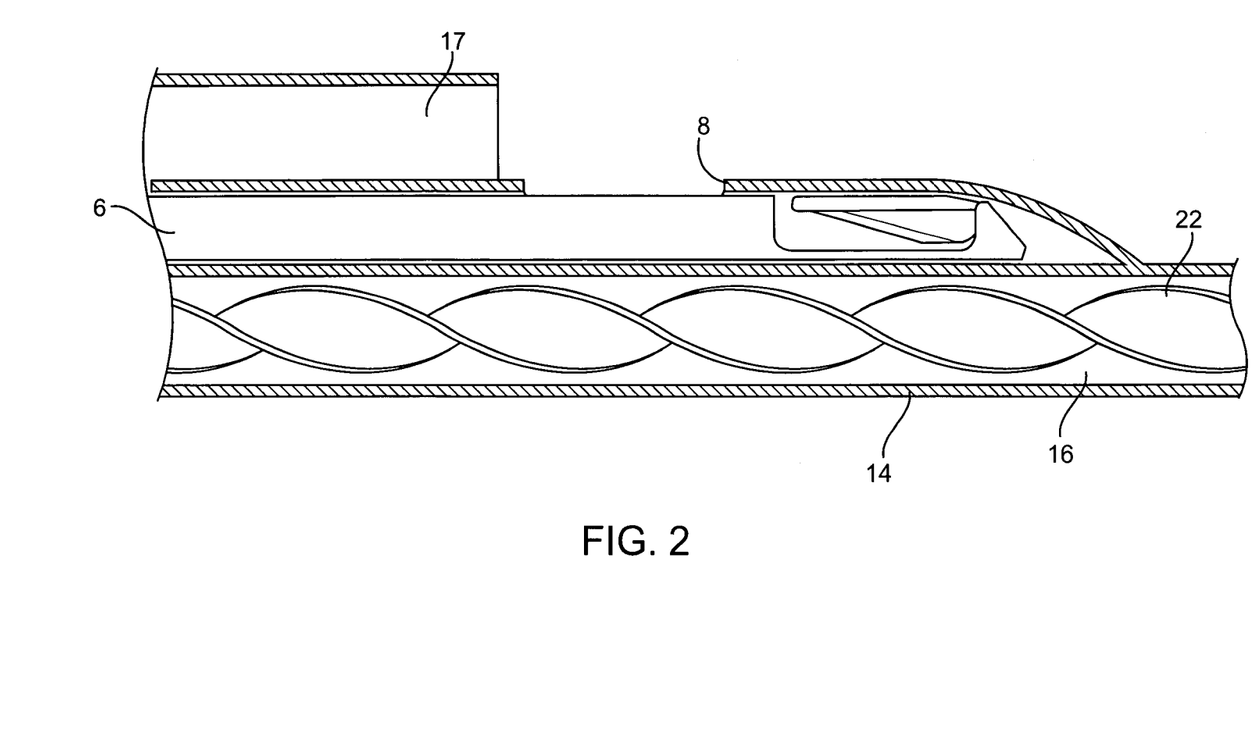
FIG. 2 is a cross-sectional view of the device of FIG. 1 with the cutting element collapsed
Figure 3:
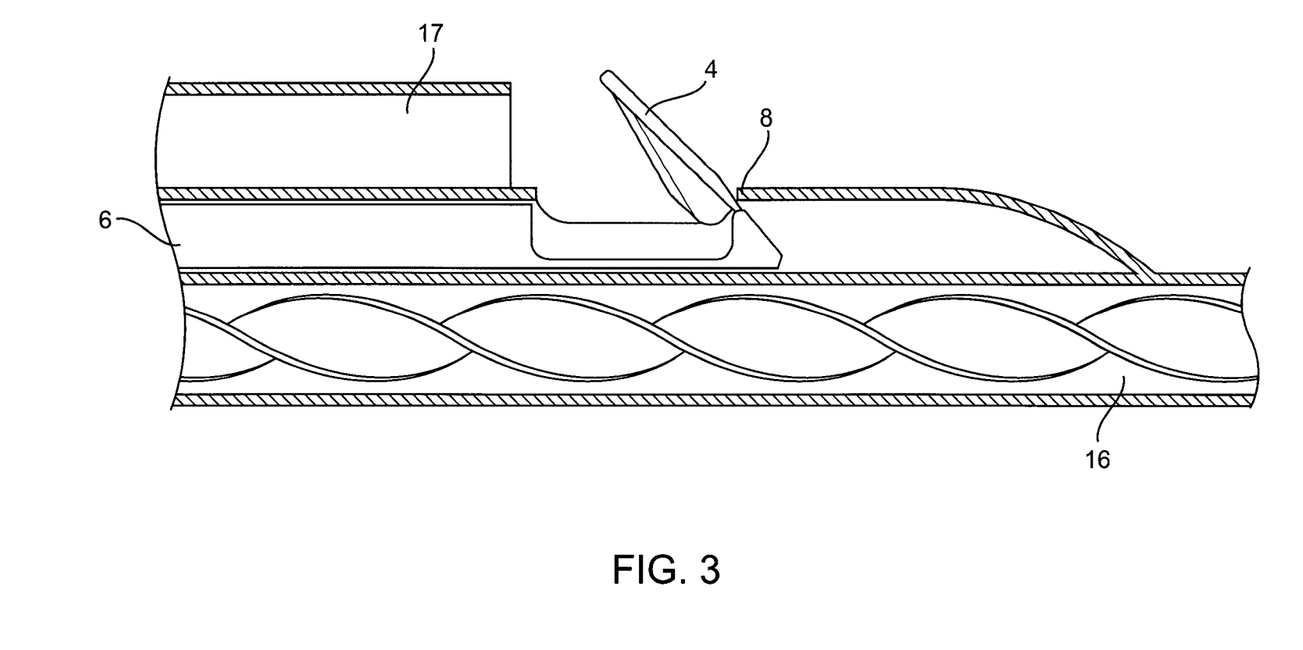
FIG. 3 is a cross-sectional view of the device of FIG. 1 with the cutting element expanded

Referring to FIGS. 1-3, a tissue cutting device 2 is shown. The device 2 is particularly suited for cutting septae while performing a liposuction procedure as described below.

Figure 4:
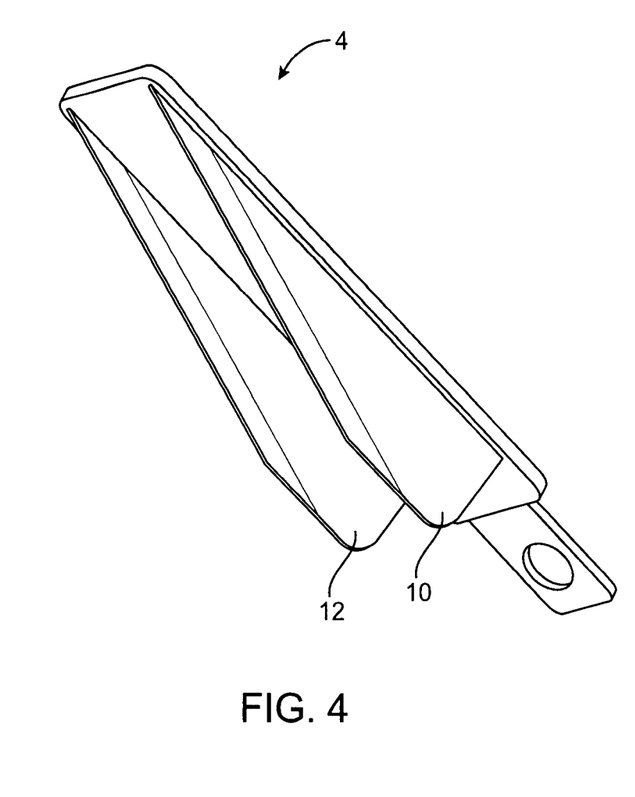
FIG. 4 is a perspective view of the cutting element

The device 2 includes a mechanical cutting element 4 to cut tissue although any other suitable cutting element 4 may be used. The cutting element 4 is movable from the collapsed position of FIG. 2 to the expanded or cutting position of FIG. 3. The cutting element 4 is coupled to a push rod 6 which is manipulated to move the cutting element 4 between the stored and cutting positions. The cutting element 4 is naturally biased toward the expanded position and is collapsed by advancing the push rod so that the cutting element 4 engages a shoulder 8 to force the cutting element 4 back to the collapsed position as the rod 6 is advanced. Referring to FIG. 4, a perspective view of the cutting element 4 is shown. The cutting element 4 may have a first blade 10 and a second blade 12 to remove a section of the septae. Removal of a section, rather than simply cutting the septae at one location, may help to prevent the septae from reattaching during the healing process. The first and second blades 10, 12 may be separated by at least 0.5 mm. It is understood that numerous aspects of the present invention may be practiced with different cutting elements such as RF, ultrasound or laser, or a single cutting element rather than two blades without departing from the scope of the invention. Furthermore, cutting may be accomplished using blunt dissection as described further below.

The device 2 includes an elongate body 14 having a suction lumen 16 extending there through. The suction lumen 16 leads to one or more suction openings 18 along the length of the body 14. The suction lumen 16 is coupled to a source of suction so that suction may be used to draw fat and other tissue into the suction openings as is known in conventional liposuction. A rotating element 22, which may be shaped similar to an Archimedes screw, may be positioned in the suction lumen 16 to assist removal of tissue. The device 2 may also have a lumen 17 which receives a visualization device 19 (see FIG. 6) such as an endoscope 21. The lumen 17 is positioned so that the user may view the tissue captured by the cutting element 4. The visualization device 19 may also be used to inspect the tissue prior to cutting. In this manner, the user may deploy the cutting element 4 to cut septae and retract the element 4 when encountering large blood vessels or nerves. The endoscope can further allow visualization of the distal tip of the cannula, which can prevent severe complications associated with undesirably puncturing body cavities.

Figure 5:
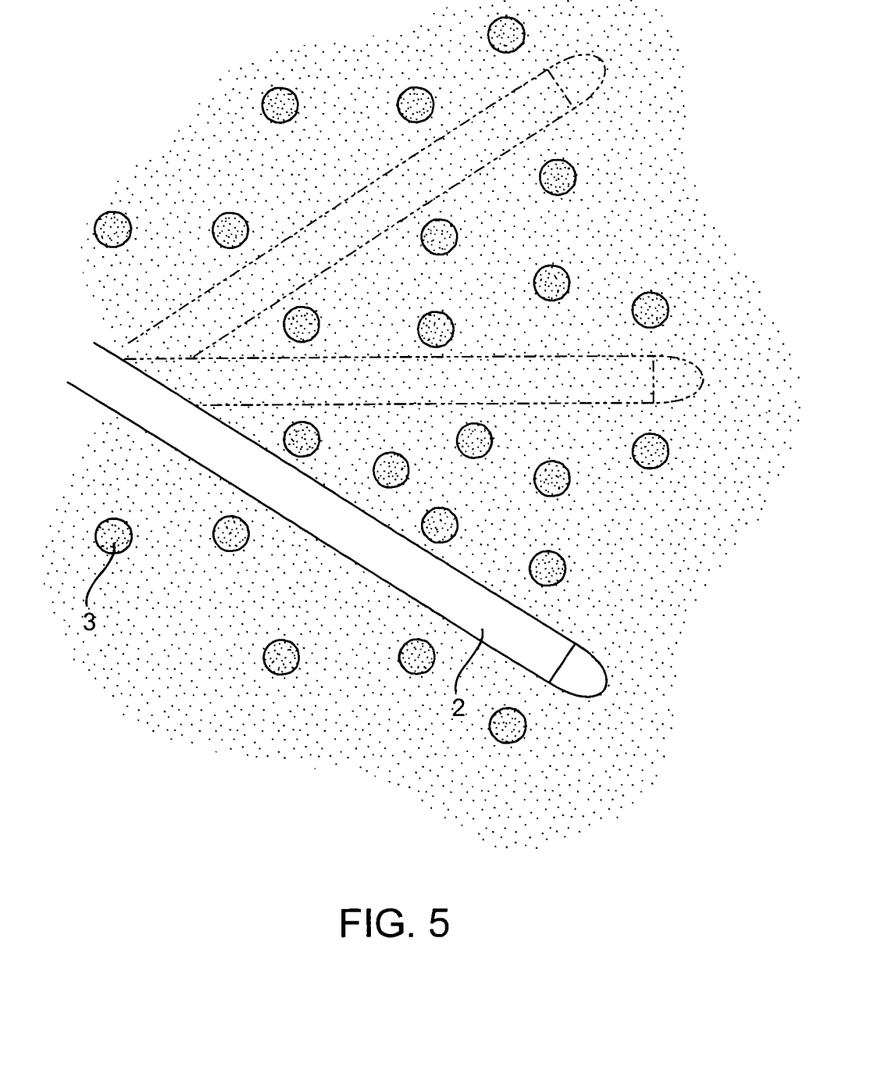
FIG. 5 shows a number of tunnels created in tissue

As mentioned above, a problem with conventional liposuction is that the liposuction wand will naturally be limited to a number of passageways or tunnels as shown in FIG. 5. It is often difficult to access the areas between these tunnels since the liposuction cannula will take the path of least resistance rather than penetrating new tissue. In particular, the septae 3 which interconnect the skin and muscle can be difficult to penetrate and can limit mobility of the cannula.

Figure 6:
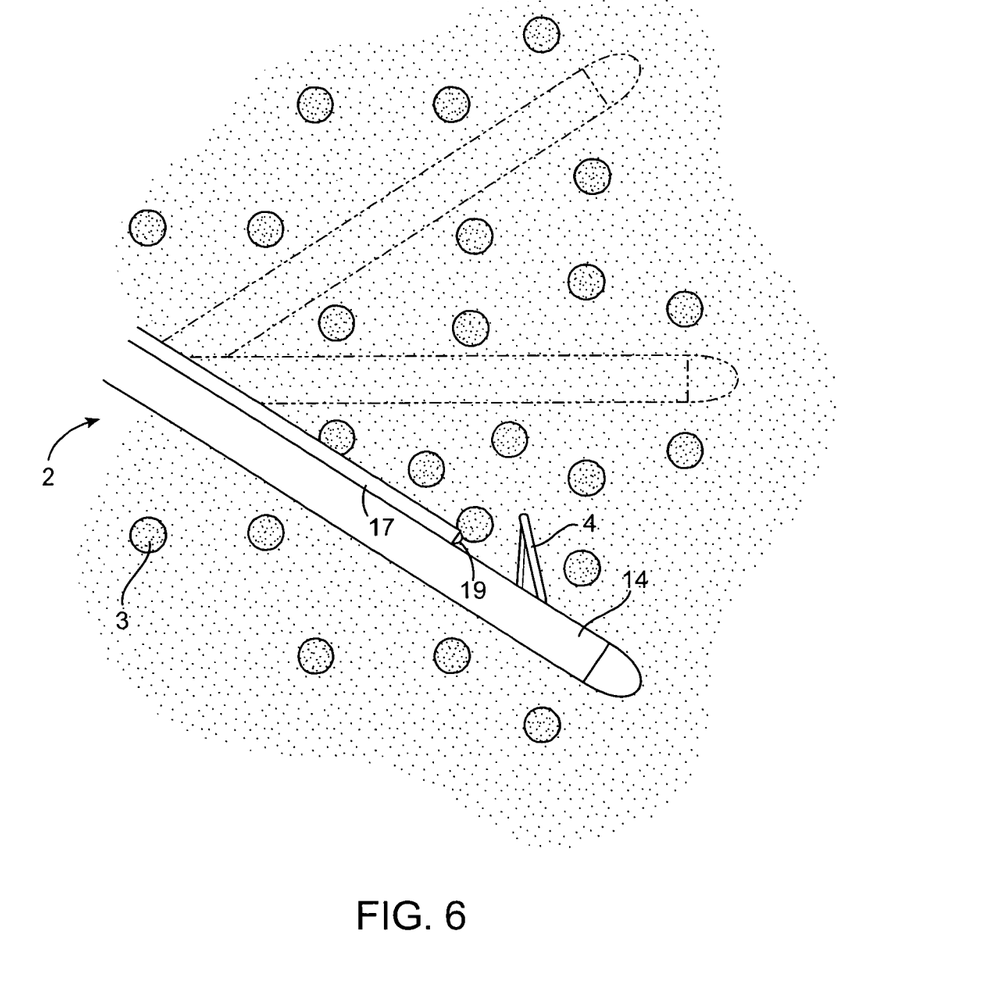
FIG. 6 shows the cutting element deployed
Figure 7:
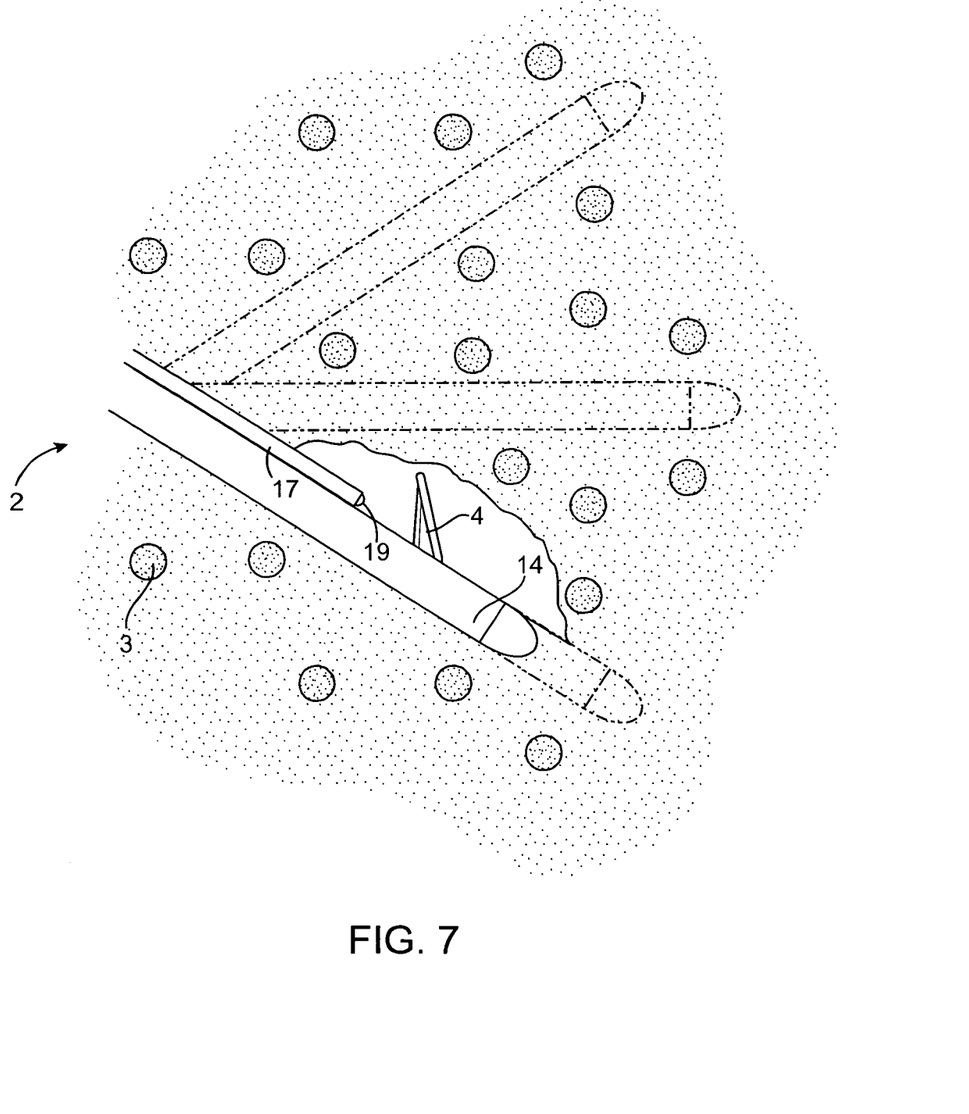
FIG. 7 shows the cutting element moved to cut tissue
Figure 8:
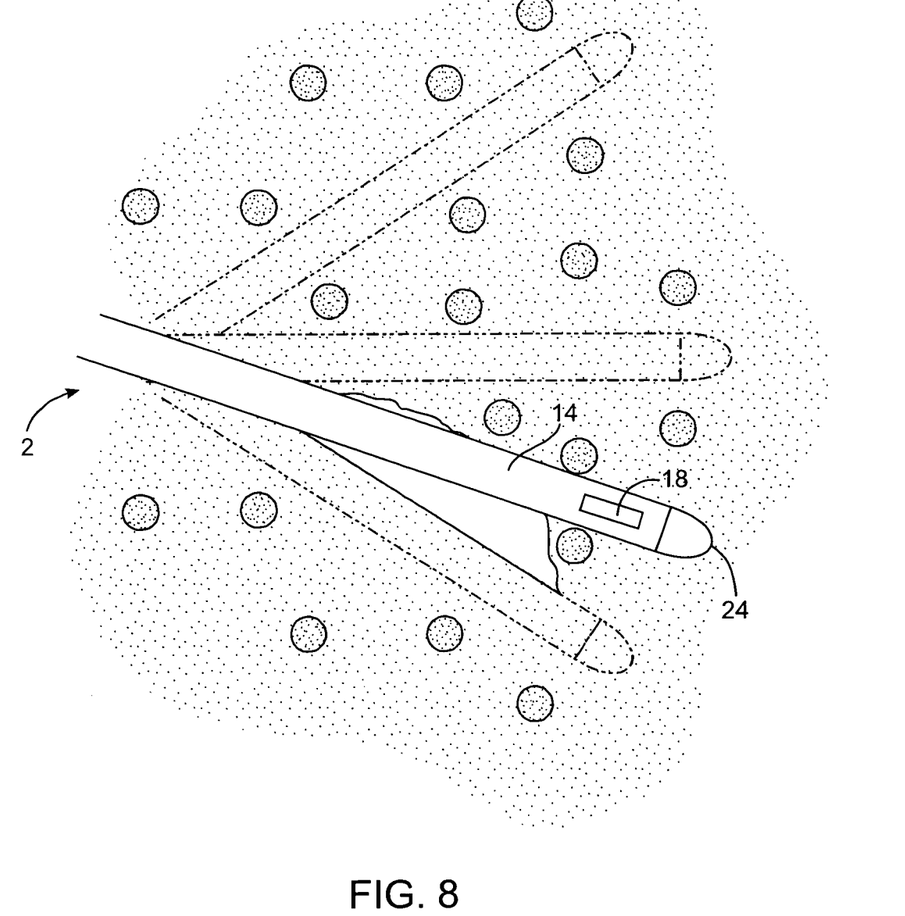
FIG. 8 shows the device advanced into the area where the tissue has been cut

The cutting element 4 of the present invention permits the user to cut tissue adjacent to the liposuction wand. In this manner, the user can position the liposuction wand in a tunnel adjacent to fat deposits that the user desires to remove but cannot reach. The cutting element 4 is positioned adjacent to the area where the user desires to remove additional fat deposits as shown in FIG. 6. The cutting element 4 is then expanded and moved proximally to cut tissue and, in particular, the septae adjacent to the body as shown in FIG. 7. The cutting element 4 is then retracted to prevent undesirable tissue damage. The body 14 is then moved so that a distal tip 24 is positioned in the area where the tissue has been cut so that the user may access the tissue area adjacent the passageway using the same incision site, as shown in FIG. 8. Although not shown, the cutting element 4 can also be distally-oriented, as opposed to proximally-oriented as shown in FIGS. 6 through 8, in which case it is moved distally to cut tissue.

Figure 9:
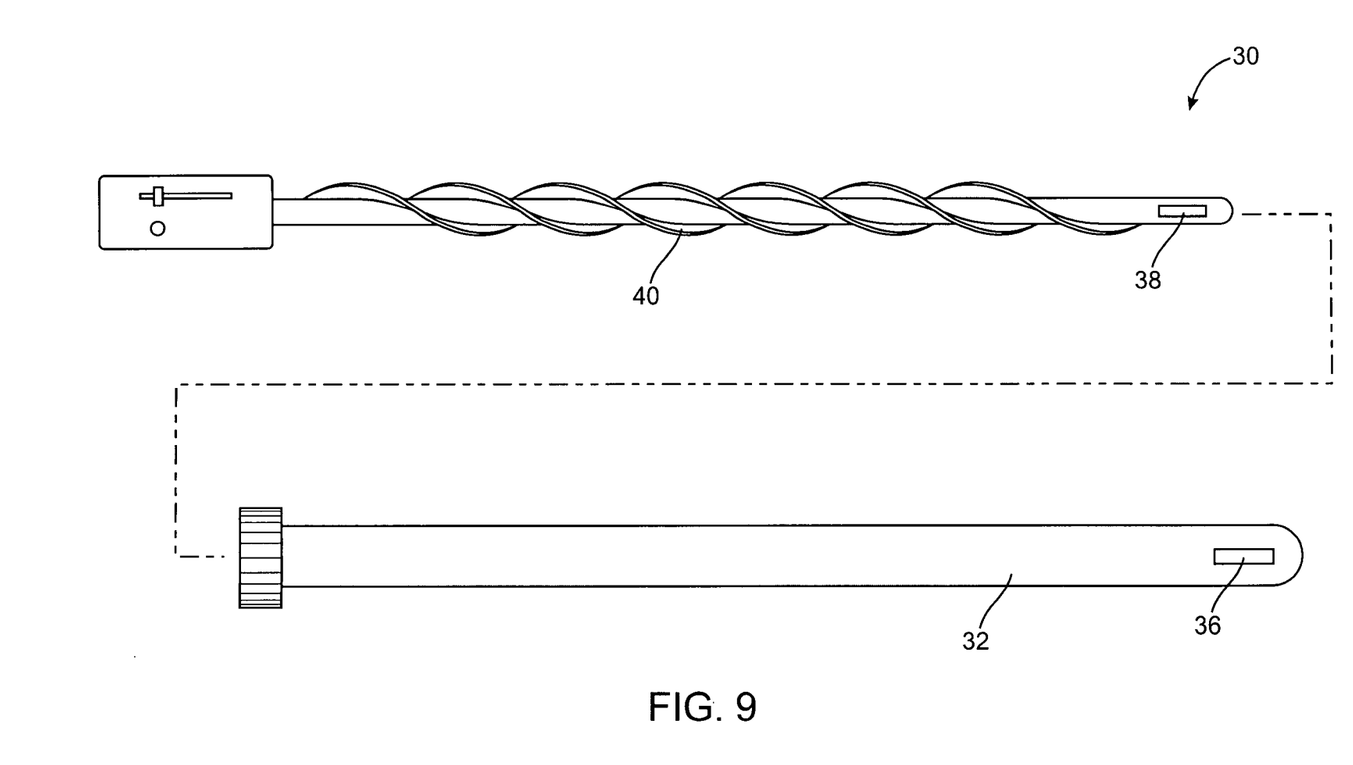
FIG. 9 shows another device for cutting tissue
Figure 10:
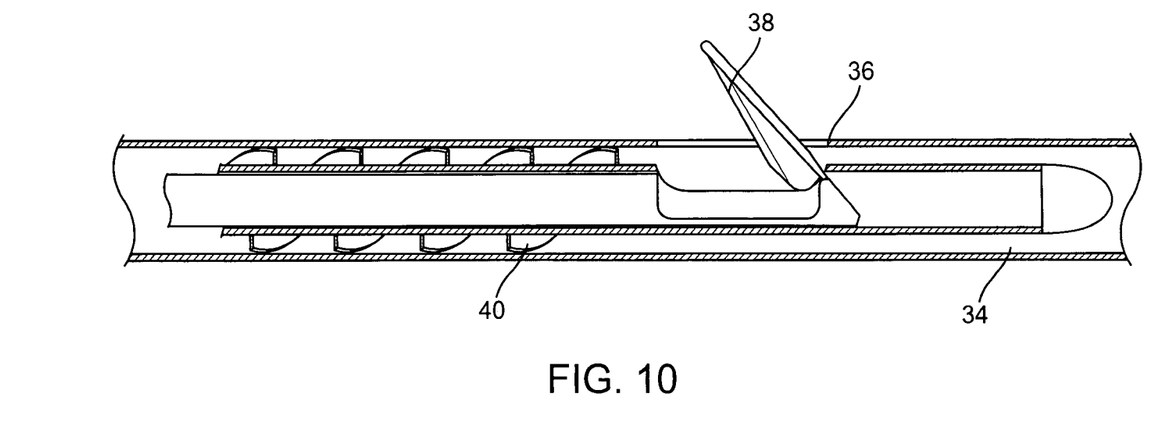
FIG. 10 shows a cross-sectional view of the device of FIG. 9 with the cutting element expanded
Figure 11:
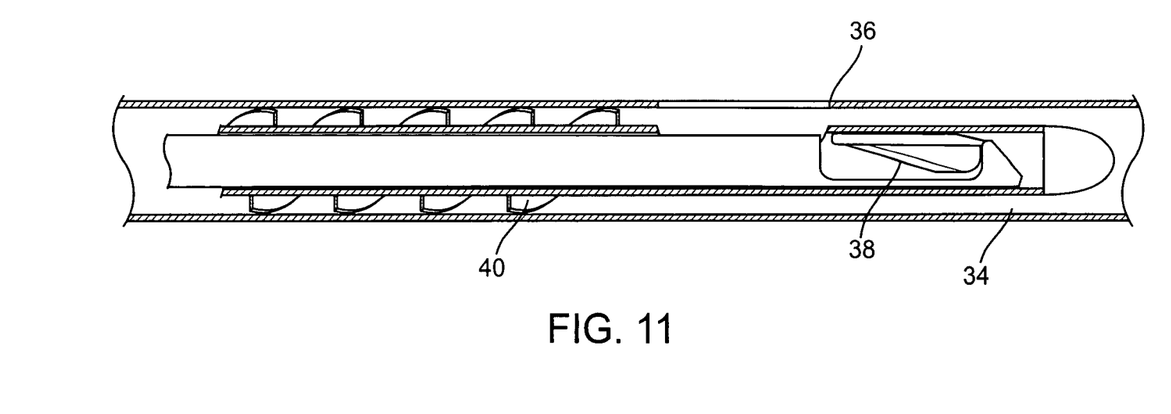
FIG. 11 shows a cross-sectional view of the device of FIG. 9 with the cutting element collapsed

Referring to FIGS. 9-11, another device 30 is shown for cutting tissue which may be used in combination with a separate liposuction cannula. The device 30 includes a body 32 having a suction lumen 34 and one or more suction openings 36 which are used to remove fat and other tissue as described above. The device 30 also includes a cutting element 38 positioned inside the suction lumen 34. The cutting element 38 is movable from a position contained within suction lumen 34 to a position outside the suction lumen 34. The cutting element 38 may also be used to enhance withdrawal of the material through the suction lumen 34. To this end, the cutting element 38 may include a screw-like exterior surface 40 which enhances withdrawal of material when the exterior surface 40 is rotated. The cutting element 38 is similar to the cutting element 4 and the description of the cutting element 4 is applicable to the cutting element 38.

An advantage of the device 30 of FIGS. 9-11 is that the cutting element 38 may be advanced and withdrawn within the suction lumen 34 as needed. This permits the user to undertake a conventional liposuction procedure and, at the appropriate time, the user may advance the cutting element 38 within the suction lumen 34 so that that tissue may be cut. The cutting element 38 may also be advanced into the suction lumen 34 to enhance withdrawal of the tissue by rotating the exterior screw-like surface 40 to draw material proximally. The cutting element 38 may also be completely removed from the cannula 32 as well.

Figure 12:
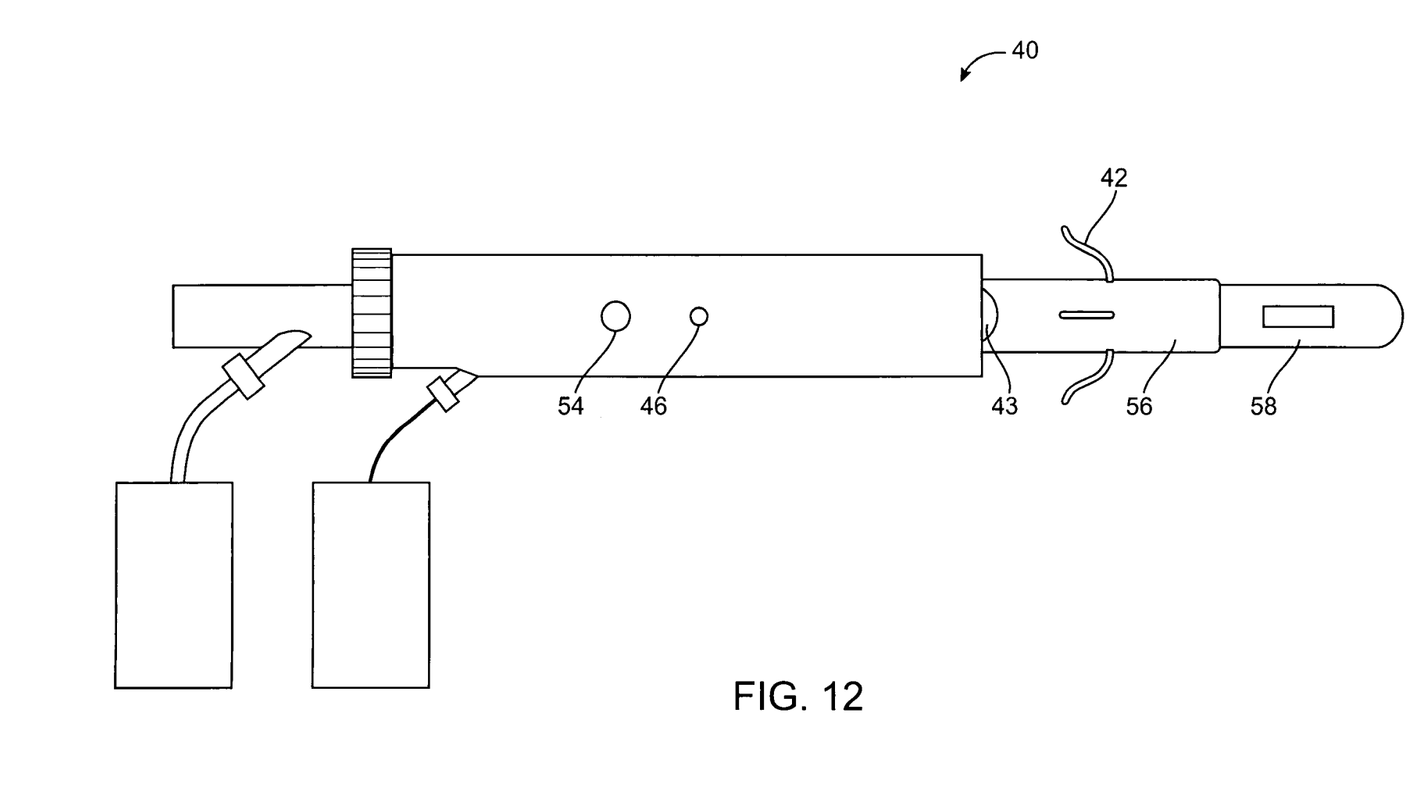
FIG. 12 shows another device for cutting tissue.
Figure 13:
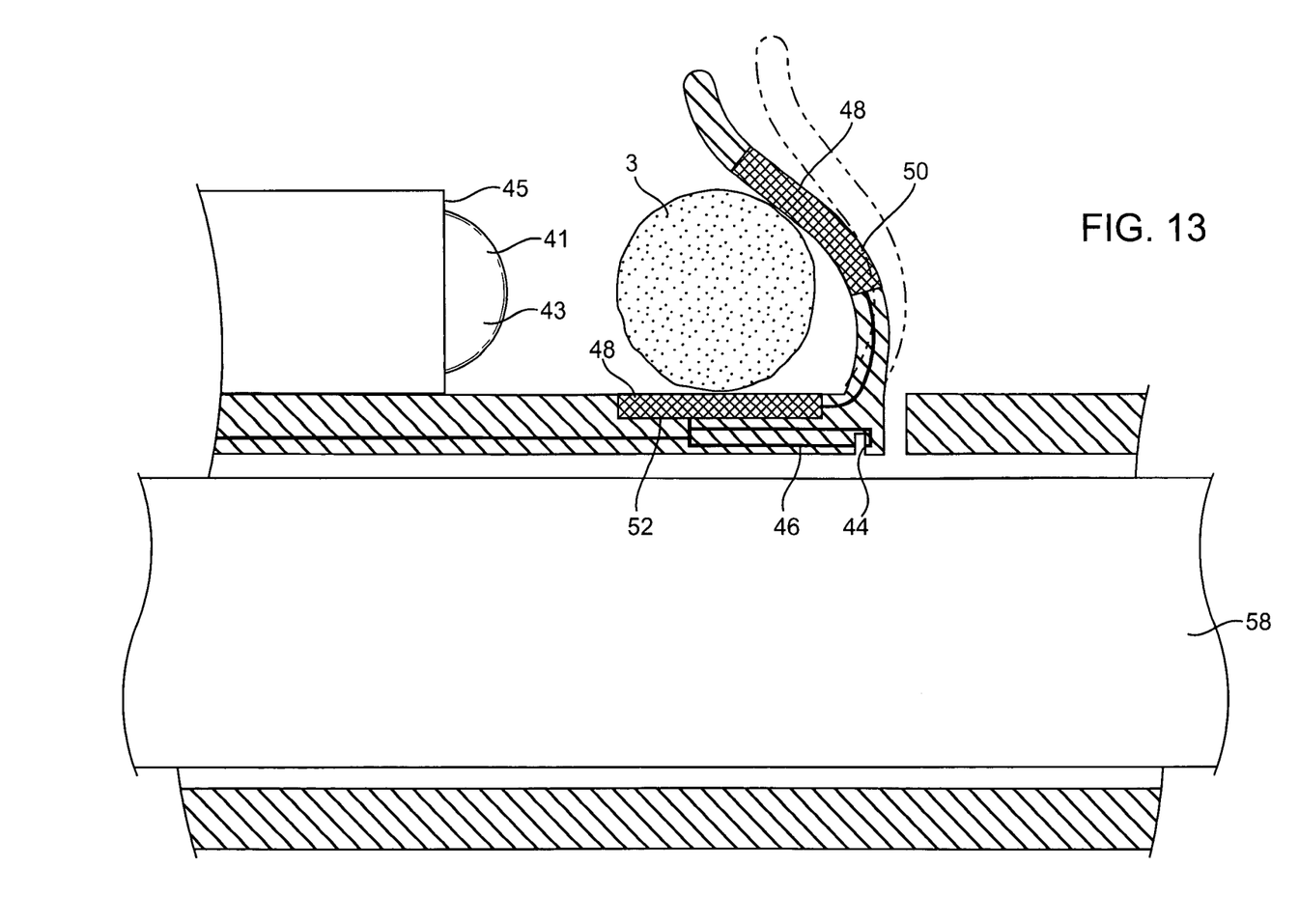
FIG. 13 is a cross-sectional view of a deflecting element and the cutting element of the device of FIG. 12
Figure 14:
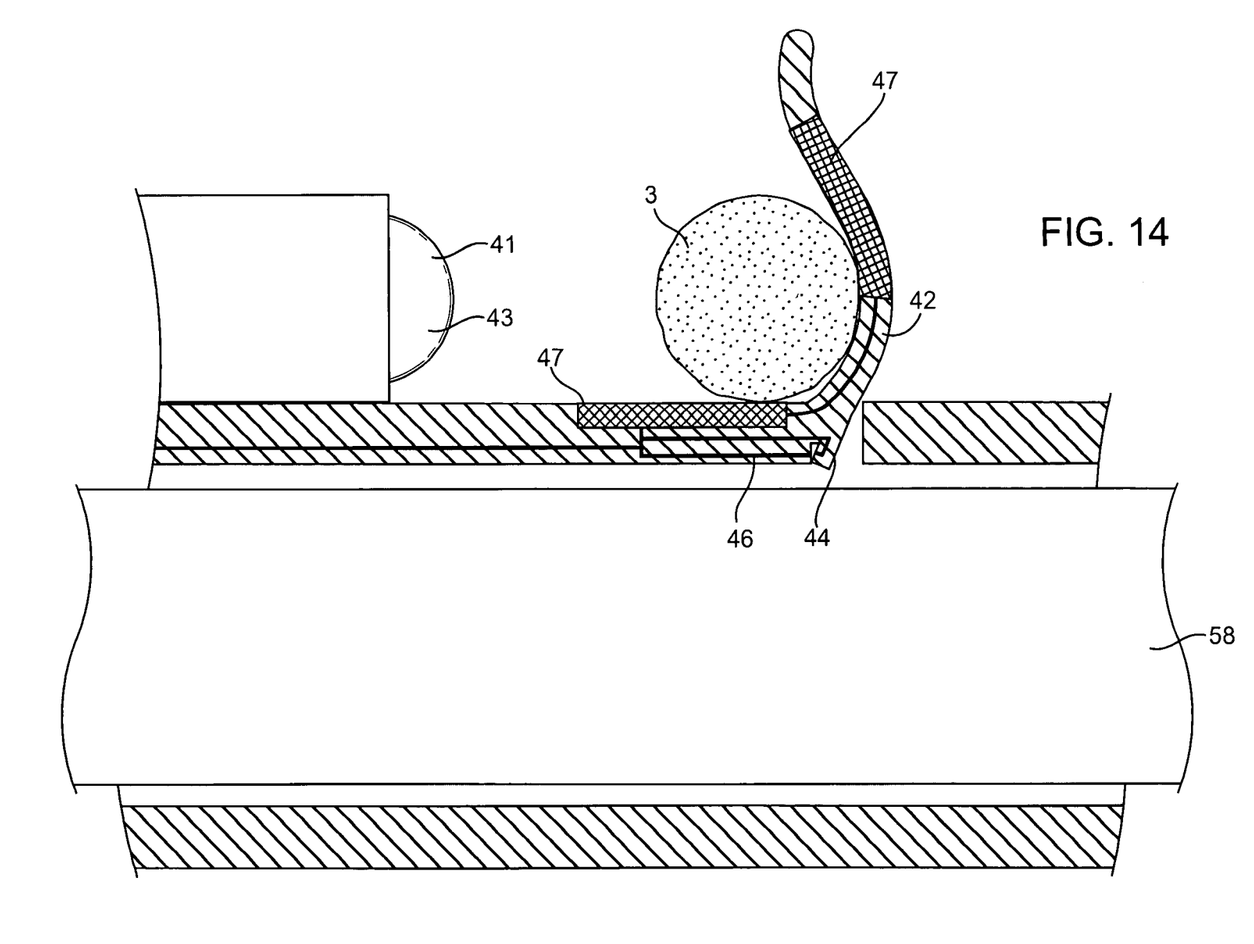
FIG. 14 shows the element of FIG. 13 deflected by a septae.

Referring to FIGS. 12-14, another tissue cutting device 40 is shown. The tissue cutting device 40 has one or more elements 42 which can be deflected as the cutting device 40 is moved through tissue. The embodiment of FIG. 12 has four elements 42 positioned at 90 degrees to one another around the body of the device 40. Spacing the elements 42 in this manner reduces the need to orient the device 40 in order to capture septae. When fewer elements 42 are used, the element(s) 42 are oriented to capture tissue which extends between the skin and muscle when moved through tissue. The element 42 loosely captures material with a hook-like structure. The element 42 can be deflected from the solid line position to the dotted line position of FIG. 13. Deflection of the element 42 may be used to distinguish relatively robust structures, such as septae, from softer tissues, such as blood vessels and nerves. Softer structures, such as blood vessels and nerves, may not be rigid enough to deflect the element and may be able to slip around the end of the relatively open hook-like element 42. The hook 42 may have smooth surfaces and transitions to minimize trauma to tissue and permit softer tissues to flow around the hook if the tissue is not robust enough to deflect the element. The element 42 may take any other suitable shape such as a V-shape.

Deflection of the element 42 may be recognized in any suitable manner. For example, a first contact point 44 on the element 42 may move into engagement with a second contact 46 as shown in FIG. 14. Of course, any other method of determining whether the element 42 has been deflected may be used. Furthermore, it is understood that deflection of the element 42 represents a threshold force required to move the element 42. As such, any other force-sensing element could be used including a piezoelectric element or a spring. The device 40 may also include a visualization device 41, such as an endoscope 43, to observe the tissue which has been trapped by the element 42. In this manner, the user may inspect the tissue which has been trapped prior to cutting. If the user does not want to cut the tissue which has been trapped, the user may simply manipulate the device 40 by gently rotating and/or advancing the device 40 to release the tissue which has been trapped. The endoscope 43 may be integrally formed with the device 40 or contained within a lumen 45.

If the element 42 is deflected as shown in FIG. 14, an indicator 46 on the device 40 may indicate to the user that the element 42 has been deflected. At this time, the user may activate a cutting mechanism 46 to sever or cut the material captured by the element 42. The cutting mechanism 47 may be any suitable cutting mechanism with FIG. 13 showing an RF cutting element 48 but may also be an ultrasound element which delivers ultrasonic energy to cut the tissue. The RF cutting element 48 has a first electrode 50 and a second electrode 52 for bipolar RF but may be configured for monopolar RF as well. The device 40 may operate to automatically activate the cutting mechanism 47 once the element 42 has been deflected or may require the user to activate the cutting element 47 using a push-button 54 or other suitable actuator.

The element 42 may be coupled to a sleeve 56 which extends over a liposuction cannula 58. As such, the user may elect when, and if, the element 42 is used if at all. The sleeve 56 also permits the user to move the cutting element 48 longitudinally along the cannula 58 so that the cutting mechanism 48 may be used to selectively release septae without having to move the cannula as described above.

The element 42 may also be used for blunt dissection of tissue. The element 42 will capture and cut the septae by application of sufficient force to rupture the septae. The user may inspect the tissue using the visualization device 41 to distinguish septae from other tissue structures as discussed above before cutting tissue. Without the use of a visualization device, the user may also tug on the captured tissue to see if it is strongly connected to the skin. By evaluating the effect on the skin surface, tissues desired to be cut can be differentiated from those which are undesirable to cut.

Figure 15:
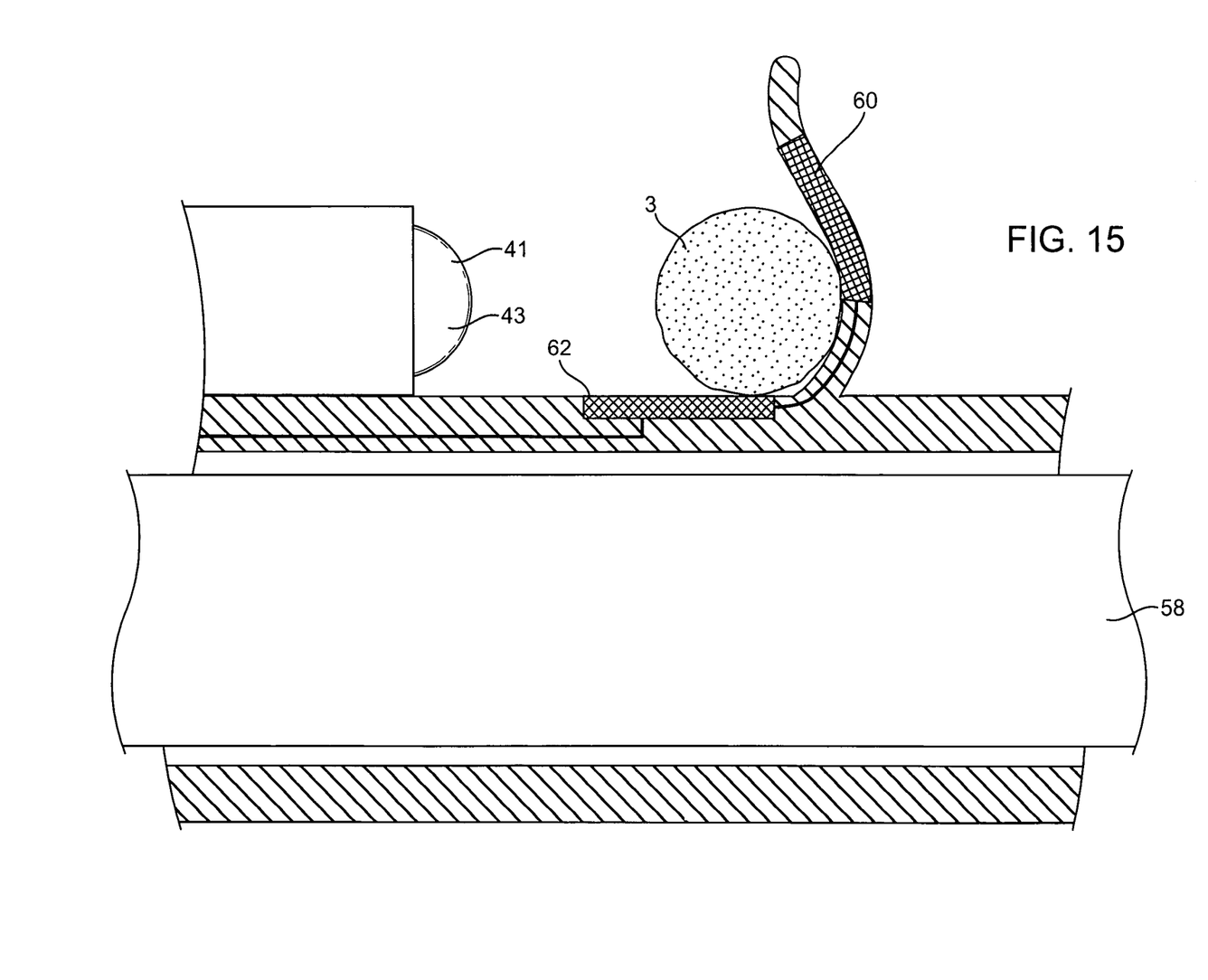
FIG. 15 shows another element which may be used with the device of FIG. 9.

Another way to distinguish structures desired or permissible to be cut such as septae and fat from tissues undesirable to affect, such as blood vessels and nerves, is to differentiate structures by their electrical characteristics. Referring to FIG. 15, a first electrode 60 and a second electrode 62 can be used in a bipolar configuration to measure electrical impedance of captured tissue. The electrode or electrodes 60, 62 can also be configured for monopolar measurements, which would require a reference electrode elsewhere on the subject. The same electrodes 60, 62 can be used to enact the cutting of the tissue. Operation and use of the elements 60, 62 may be the same as described above in connection with FIG. 9. For example, the indicator 46 may be used to determine whether the electrical impedance measured by the electrodes 60, 62 is within a threshold range which may help to distinguish blood vessels and nerves from septae. The device may operate to automatically activate cutting of the tissue or may require the user to activate the cutting element as described above.

The present invention has been described in connection with preferred embodiments, however, it is understood that numerous modifications could be made to the preferred embodiments without departing from the scope of the invention. For example, any cutting mechanism may be used to cut septae without departing from the scope of the invention.

The invention claimed is:

1. A method of dissecting septae which extend between the skin and muscle, comprising the steps of:
   providing a septae cutting device having a body and a sensing element;
   moving the body through tissue in an area between skin and muscle so that tissue contacts the sensing element as the body is moved, the sensing element being affected an amount when contacting septae to distinguish septae from other tissue;
   cutting septae, which affect the sensing element the amount, wherein tissue which does not affect the sensing element the amount is not cut;
   wherein the cutting step is initiated after the amount is measured and the amount is measured before beginning the cutting step.

2. The method of claim 1, wherein:
   the sensing element measures deflection.

3. The method of claim 1, wherein:
the cutting step is carried out automatically when the sensing element measures the amount.

4. The method of claim 1, wherein:
the cutting step is carried out using radiofrequency energy.

5. The method of claim 1, wherein:
the cutting step is carried out using ultrasonic energy.

6. The method of claim 1, wherein:
the providing step is carried out with the septae cutting device having an indicator and an actuator, the indicator indicating to the user when the sensing element has measured the amount during the moving step;
the cutting step is carried out when the user activates the actuator.

* * * * *